United States Patent
Fischer et al.

(10) Patent No.: US 10,539,515 B2
(45) Date of Patent: Jan. 21, 2020

(54) COMPUTED TOMOGRAPHIC SYSTEM CALIBRATION

(71) Applicant: GE Inspection Technologies, LP, Lewistown, PA (US)

(72) Inventors: Andreas Fischer, Wunstorf (DE); Nils Rothe, Wunstorf (DE); Alexander Suppes, Wunstorf (DE); Eugen Trapet, Sarria (ES)

(73) Assignee: GE Inspection Technologies, LP, Lewistown, PA (US)

( * ) Notice: Subject to any disclaimer, the term of this patent is extended or adjusted under 35 U.S.C. 154(b) by 119 days.

(21) Appl. No.: 15/941,310

(22) Filed: Mar. 30, 2018

(65) Prior Publication Data

US 2019/0302036 A1 Oct. 3, 2019

(51) Int. Cl.
*G01N 23/046* (2018.01)
*G01T 7/00* (2006.01)

(52) U.S. Cl.
CPC ........... *G01N 23/046* (2013.01); *G01T 7/005* (2013.01); *G01N 2223/3035* (2013.01); *G01N 2223/3306* (2013.01); *G01N 2223/419* (2013.01)

(58) Field of Classification Search
CPC .............................................. G01N 2223/3035
See application file for complete search history.

(56) References Cited

U.S. PATENT DOCUMENTS

| | | | | |
|---|---|---|---|---|
| 5,442,674 A | * | 8/1995 | Picard | A61B 6/583 378/18 |
| 2004/0245447 A1 | * | 12/2004 | Karasawa | A61B 6/583 250/252.1 |
| 2013/0230150 A1 | * | 9/2013 | Weiss | A61B 6/4233 378/207 |
| 2014/0056495 A1 | * | 2/2014 | Janssens | A61B 6/582 382/128 |
| 2016/0051219 A1 | * | 2/2016 | Shimada | A61B 6/502 378/37 |

* cited by examiner

*Primary Examiner* — Yara B Green
(74) *Attorney, Agent, or Firm* — Mintz Levin Cohn Ferris Glovsky and Popeo, P.C.

(57) ABSTRACT

Method and apparatus are provided for calibration or verification of accuracy specification of a computed tomographic system. In one embodiment, the apparatus can include a base structure, a first set of test objects arranged along a first axis and coupled to the base structure, and a second set of test objects arranged along a second axis and coupled to the base structure. The first set of test objects and the second set of test objects have a first geometry. The apparatus can also include a third set of test objects and a fourth set of test objects. The third set of test objects, and the fourth set of test objects have a second geometry different from the first geometry. Locations of the first, second third and fourth set of test objects are spatially fixed with respect to the base structure. The apparatus is a test specimen adapted for calibration or accuracy verification of computed tomography system.

20 Claims, 11 Drawing Sheets

COMPUTED TOMOGRAPHIC SYSTEM CALIBRATION

BACKGROUND

Industrial computed tomography (CT) scanning systems can be commonly used to produce three-dimensional representations of industrial parts. For example, industrial CT scanning systems can facilitate nondestructive internal inspection of industrial machine parts. As a result, CT scanning can be used for flaw detection, assembly analysis, and failure analysis of machine parts. CT scanning involves irradiating a machine part with an electromagnetic radiation (e.g., X-ray) and detecting a portion of the radiation that is modified (e.g., transmitted, reflected, and the like) by the machine part. This process is repeated for various orientations of the machine part and at various locations of the machine part with respect to the source of the radiation. Based on detection of multiple images of the machine parts (e.g., for the various orientations and locations), a three-dimensional representation of the machine part can be generated (e.g., by a computing device).

CT scanning systems have to be calibrated (e.g., prior to a measurement) for generating accurate three-dimensional representations. System calibration can involve assessment of dimensional measurement capabilities and measurement uncertainty (e.g., length measurement errors) of the scanning system. This can be done by scanning a measurement phantom having known physical properties (e.g., shape, size, material composition, and the like) and calculating measurement uncertainty based on the generated-three dimensional representation and the known geometry of the phantom.

Guidelines such as VDI/VDE 2630-1.3 and ISO draft 10360-11 provide guidelines for specifying the accuracy of x-ray CT scanning systems. For example, according to VDI 2630 guidelines, length measurements of the phantom are performed in three directions (e.g., horizontal, diagonal and vertical), and in each direction there are at least five preferably evenly distributed distances. Further, according to the VDI 2630 guidelines, length measurements of the phantom should be performed at two locations (e.g., resulting in two magnification) and the longest length measurement should be at least 66% of the length of a scan volume. CT system operators can verify whether the CT system reaches the specified accuracy with a process and a phantom satisfying the VDI/VDE 2630-1.3 and ISO draft 10360-11 guidelines.

The phantom used in the calibration of CT scanning systems can facilitate the length measurements described in the VDI 2630 guidelines. For example, the phantom can include geometric markers that allow for the prescribed length measurements. A commonly used phantom is a ball bar that includes a bar that can rotate about an axis and to which several balls are rigidly attached. In order to satisfy the requirements of the VDI 2630 guidelines, the ball bar is placed at two locations (e.g., with respect to the X-ray source of the CT scan system), and at each location, the orientation of the bar is altered. For example, the bar needs to be oriented along a vertical direction, a horizontal direction and a diagonal direction at each of the two locations. This can be done by manually varying the orientation of the bar. However, adjusting the ball bar by hand during the calibration process can introduce errors in the calibration and can slow the calibration process.

SUMMARY

In general, apparatus, systems, methods and article of manufacture for calibrating computed tomography system are provided.

In one embodiment, the apparatus can include a base structure, a first set of test objects arranged along a first axis and coupled to the base structure, and a second set of test objects arranged along a second axis and coupled to the base structure. The first set of test objects and the second set of test objects can have a first geometry. The apparatus can also include a third set of test objects arranged along a third axis and coupled to the base structure, and a fourth set of test objects arranged along a fourth axis and coupled to the base structure. The third set of test objects and the fourth set of test objects can have a second geometry different from the first geometry. Locations of the first set of test objects, the second set of test objects, the third set of test objects, and the fourth set of test objects can be spatially fixed with respect to the base structure. The apparatus is a test specimen adapted for calibration and/or accuracy verification of computed tomography system.

One or more of the following features can be included in any feasible combination.

In one embodiment, the base structure can be a ceramic plate. In another embodiment, the first axis can be parallel to the third axis, and the second axis can be parallel to the fourth axis. In yet another embodiment, the first set of test objects and the second set of test objects can be spherical having a first radius; and the third set of test objects and the fourth set of test objects can be spherical having a second radius different from the first radius.

In one embodiment, the first set of test objects, the second set of test objects, the third set of test objects and the fourth set of test objects can include ruby and/or ceramic. In another embodiment, the first radius can be 5 mm, and the second radius can be 2 mm. In yet another embodiment, the base structure, the first set of test objects, the second set of test objects; the third set of test objects, and the fourth set of test objects can be configured to receive X-ray radiation from a source and modify a portion of the received X-ray radiation.

In one embodiment, the apparatus can further include a pair of test objects having the first geometry and arranged along a fifth axis, and a first test object from the first set of test objects and a second test object arranged along a sixth axis. The fifth axis and the sixth axis can be parallel, and the second test object can have the first geometry. In another embodiment; eleven test objects can have the first geometry, and eleven test objects can have the second geometry.

In one embodiment, the apparatus can further include a seventh set of test objects arranged along a seventh axis and coupled to the base structure, and an eighth set of test objects arranged along an eighth axis and coupled to the base structure. The seventh set of test objects can have the first geometry, and the eighth set of test objects can have the second geometry. In another embodiment, the first geometry can be the shape of the first set of test objects and the second geometry can be the shape of the second set of test objects.

In one embodiment, a method for determining length measurement error of a computed tomography device can include placing a computed tomography test specimen at a first location. The computed tomography test specimen can be configured to receive an X-ray beam and transmit a modified beam. The modified beam can include a portion of the received X-ray beam. The method can also include rotating the computed tomography test specimen about a rotation axis, and detecting a first plurality of images associated with the modified beams at various orientations of the computed tomography test specimen during rotation about the rotation axis at the first location. The method can further include placing the computed tomography test specimen at a second location, and rotating the computed tomography test specimen about the rotation axis. The method can also include detecting a second plurality of images associated with modified beams at various orientation of the computed tomography test specimen during rotation about the rotation axis at the second location. The method further includes determining a length measurement error of a computed tomography device based on the first plurality of images and the second plurality of images. The method can also include providing data characterizing the determined length measurement error. The computed tomography test specimen can include a base structure, a first set of test objects arranged along a first axis and coupled to the base structure, and a second set of test objects arranged along a second axis and coupled to the base structure. The first set of test objects and the second set of test objects can have a first geometry. The test specimen can also include a third set of test objects arranged along a third axis and coupled to the base structure, and a fourth set of test objects arranged along a fourth axis and coupled to the base structure. The third set of test objects and the fourth set of test objects can have a second geometry different from the first geometry. Locations of the first set of test objects, the second set of test objects, the third set of test objects, and the fourth set of test objects can be spatially fixed with respect to the base structure. The test specimen can be adapted for calibration and/or verification of accuracy of the computed tomography system.

In one embodiment, the base structure can be a ceramic plate. In another embodiment, the rotation axis of the computed tomography test specimen can be perpendicular to the path of the X-ray beam. In yet another embodiment, the first set of test objects and the second set of test objects are spherical having a first radius, and the third set of test objects and the fourth set of test objects are spherical having a second radius different from the first radius.

In one embodiment, the spheres having the first radius and the spheres having the second radius can include ruby and/or ceramic. In another embodiment, the first radius can be 5 mm, and the second radius can be 2 mm. In yet another embodiment, the computed tomography test specimen can further include a pair of test objects having the first geometry and arranged along a fifth axis, a first test object from the first set of test objects and a second test object arranged along a sixth axis. The fifth axis and the sixth axis can be parallel and the second test object has the first geometry.

In one embodiment, the computed tomography test specimen can further include a seventh set of test objects arranged along a seventh axis and coupled to the base structure, and an eighth set of test objects arranged along an eighth axis and coupled to the base structure. The seventh set of test objects can have the first geometry, and the sixth set of test objects can have the second geometry.

These and other capabilities of the disclosed subject matter will be more fully understood after a review of the following figures, detailed description, and claims.

BRIEF DESCRIPTION OF TFIZ FIGURES

These and other features will be more readily understood from the following detailed description taken in conjunction with the accompanying drawings, in which.

DETAILED DESCRIPTION

Certain exemplary embodiments will now be described to provide an overall understanding of the principles of the structure, function, manufacture, and use of the systems, devices, and methods disclosed herein.

Industrial computer tomography (CT) systems can be calibrated for generating accurate three-dimensional representations of machine parts. Calibration and verification can be achieved by scanning a known measurement phantom at multiple locations and for multiple orientations of the phantom. However, some existing phantoms can require extensive adjusting of the phantom by hand during the calibration process because the phantom can include movable parts and/or is moved during the calibration process. This approach can introduce calibration or verification errors and can slow the calibration or verification process. The current subject matter can provide a test phantom having multiple test objects with different geometries that are fixed with respect to one another so that the calibration process can be performed with limited or no adjustment of the phantom by hand. Reducing or eliminating the occurrence of adjustment to the phantom can reduce calibration or verification error and can expedite the calibration or verification process.

Figure 1:
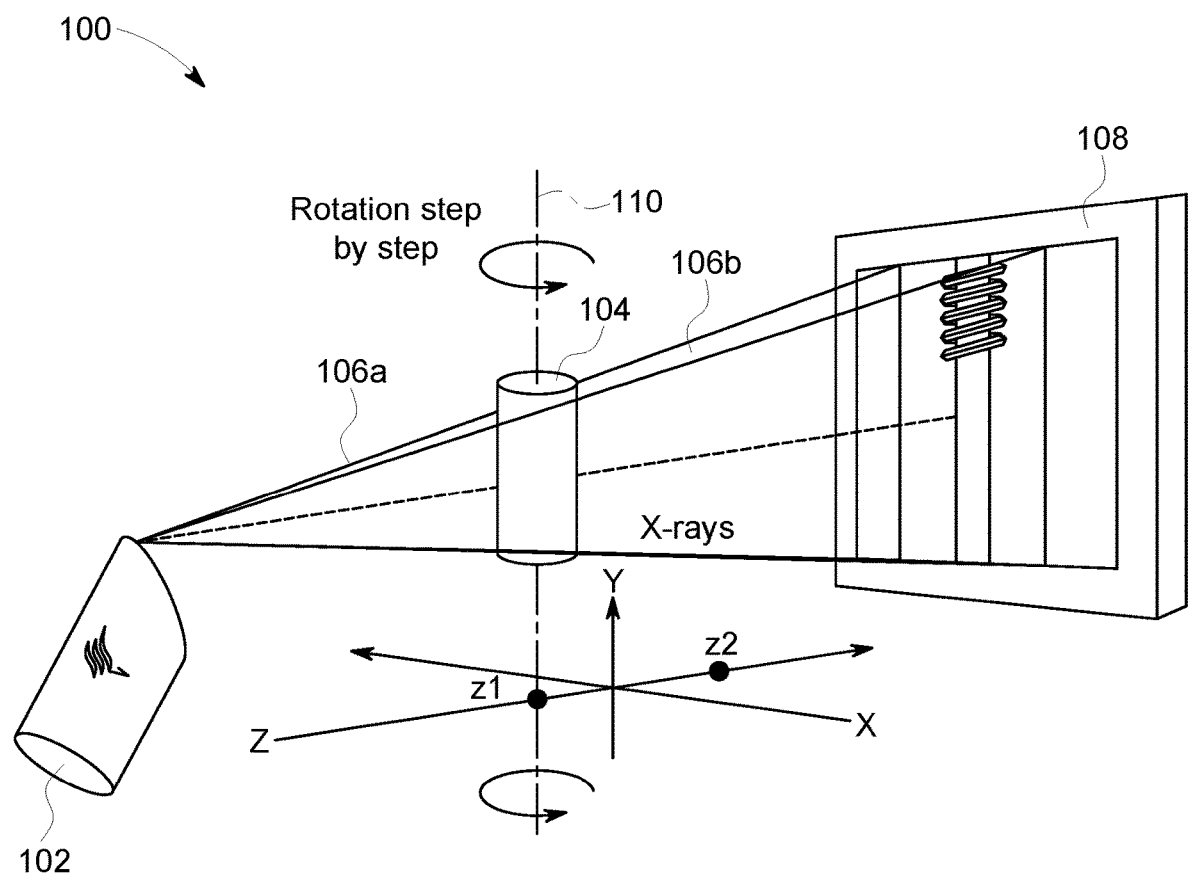
FIG. 1 is an illustration of an exemplary industrial computer tomography (CT) system.

FIG. 1 is an illustration of an exemplary industrial computer tomography (CT) system 100 that can perform non-destructive machine inspection of industrial machine parts. The system 100 includes a radiation source 102 that can illuminate an industrial machine part 104 with an electromagnetic radiation 106a (e.g., X-rays traveling along the z-axis). In one implementation, the machine part 104 can be a phantom that can allow for the calibration or verification of accuracy of the industrial CT system 100. The machine part 104 can interact with the electromagnetic radiation 106a (e.g., absorb, reflect, scatter, etc.), and can produce a modified electromagnetic radiation 106b. A detector 108 can detect the modified electromagnetic radiation 106b. This detection process can be repeated by varying the orientation between the machine part 104 and the detector 108. For example, the machine part 104 can be rotated about an axis 110 (e.g., parallel to the y-axis), and the detector 108 can detect the modified electromagnetic radiation 106b for various orientations of the machine part 104 during the rotation. Alternately or additionally, the detector 108 and the radiation source 102 can be rotated about the machine part 104 (e.g., rotated in the x-z plane about the y-axis) and the modified electromagnetic radiation 106b can be detected for various angular positions of the detector 108 and the radiation source 102. Detection of modified electromagnetic radiation 106b at various angular location can be repeated for different locations (e.g., locations between the radiation source 102 and the detector 108) of the machine part 104. For example, the location of the machine part 104 can be varied along the z-axis. A first measurement (e.g. by rotating the machine part and detecting the modified electromagnetic radiation 106b for multiple angular orientation) can be performed at location z1, and a second measurement can be performed at the location z2. The machine part 104 can be rotated (e.g., at z1, z2, and the like) by an actuator. The actuator can be an electric actuator powered by a motor that can convert electrical energy to mechanical torque which can be applied to the machine part 104. Based on the various image detections by the detector 108, a three-dimensional representation of the machine part 104 can be generated (e.g., by a computing device).

Figure 2:
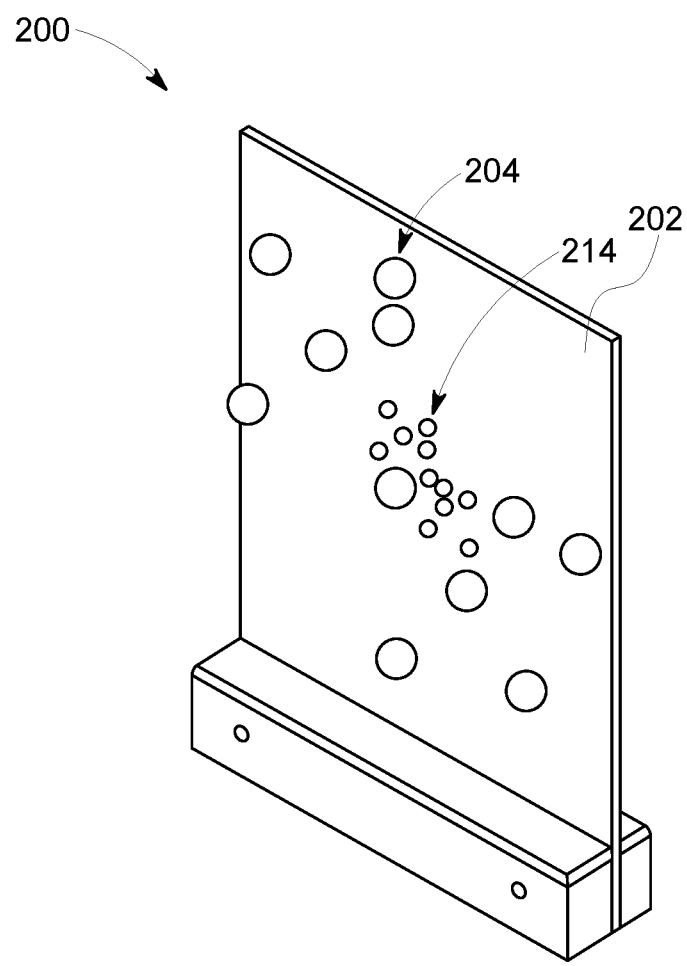
FIG. 2 is an illustration of an exemplary phantom.

FIG. 2 is an illustration of an exemplary phantom 200 that can be used for calibration or verification of a CT system (e.g., CT system 100). The phantom can include a base 202 to which multiple test objects (e.g., 204, 214, etc.) can be attached. For example, the multiple test objects can be immovably attached to the base 202 (e.g., by a mechanical connection). The test objects (e.g., 204, 214, etc.) can have various geometries (e.g., spheres with different radii) arranged along multiple axes (e.g., horizontal axis parallel to the x-z plane, vertical axis parallel to the y-axis, diagonal axis parallel to the y-z plane, and the like). The base 202 can include a ceramic (e.g., $Al_2O_3$, BN, $SiO_2$, $ZrO_2$, $Si_3N_4$) or a mixture of ceramics. The test objects 204 and 214 can include ruby and/or ceramics. In some implementations, the test objects 204 and test objects 214 can include the same material (e.g., ruby, ceramics, etc.). In other implementations, the test object 204 and test objects 214 can include different materials. The base 202, test objects 204, and test objects 214 can interact differently with an incident radiation (e.g., electromagnetic radiation 106a) due to differences in their composition, shape, and the like. CT system can be calibrated or its accuracy verified by placing the phantom 200 at a first location (e.g., at z1) between the radiation source 102 and the detector 108 rotating the phantom 200 about an axis (e.g., y axis). At various orientations of the phantom 200 during rotation, the phantom 200 can receive the electromagnetic radiation 106a and transmit the modified electromagnetic radiation 106b (which can be a portion of the received electromagnetic radiation 106a). The detector 108 can detect the modified electromagnetic radiation 106b at the various orientations of the phantom 200 and generate multiple images (e.g., images at predetermined times that correspond to predetermined orientation of the phantom 200). The phantom 200 can be placed at a second location (e.g., at z2) and the measurement of multiple images can be repeated.

The multiple images detected by the detector 108 (e.g., corresponding to location of the phantom at z1 and z2) can be used to determine location of test objects (e.g., center of spherical test objects 204, 214, etc.), distances between test objects, a length measurement error, and the like. In some implementations, distances between test objects can be calculated using $L_2$ norm (e.g., Euclidean distance). From the detected images, distances between the various test objects (e.g., distance between the various test objects 204, distance between the test objects 214) can be calculated. By comparing the calculated distances with actual test object distances (e.g., measured by the calibration laboratory), a sphere distance error or a length measurement error of the CT system can be calculated. The length measurement error can be calculated, for example, using difference in the Euclidean distance between sphere centers of the test objects (sphere distance errors), deviations in the size of test objects, deviations in the shape of the test objects, and the like.

In some implementations, the determination of the length measurement error can comply with VDI/VDE 2630-4.3 guidelines, ISO draft 10360-11 guidelines, etc. For example, to comply with the VDI 2630 guidelines, length measurements of the phantom can be performed in three directions (e.g., horizontal, diagonal and vertical), and in each directions there can be at least five preferably evenly distributed distances. The test objects 204 and 214 can be arranged on the phantom 200 to allow for length measurements (e.g., length measurements between the various test objects 204, length measurement between the test objects 214) required by the VDI 2630 guidelines.

Figure 3:
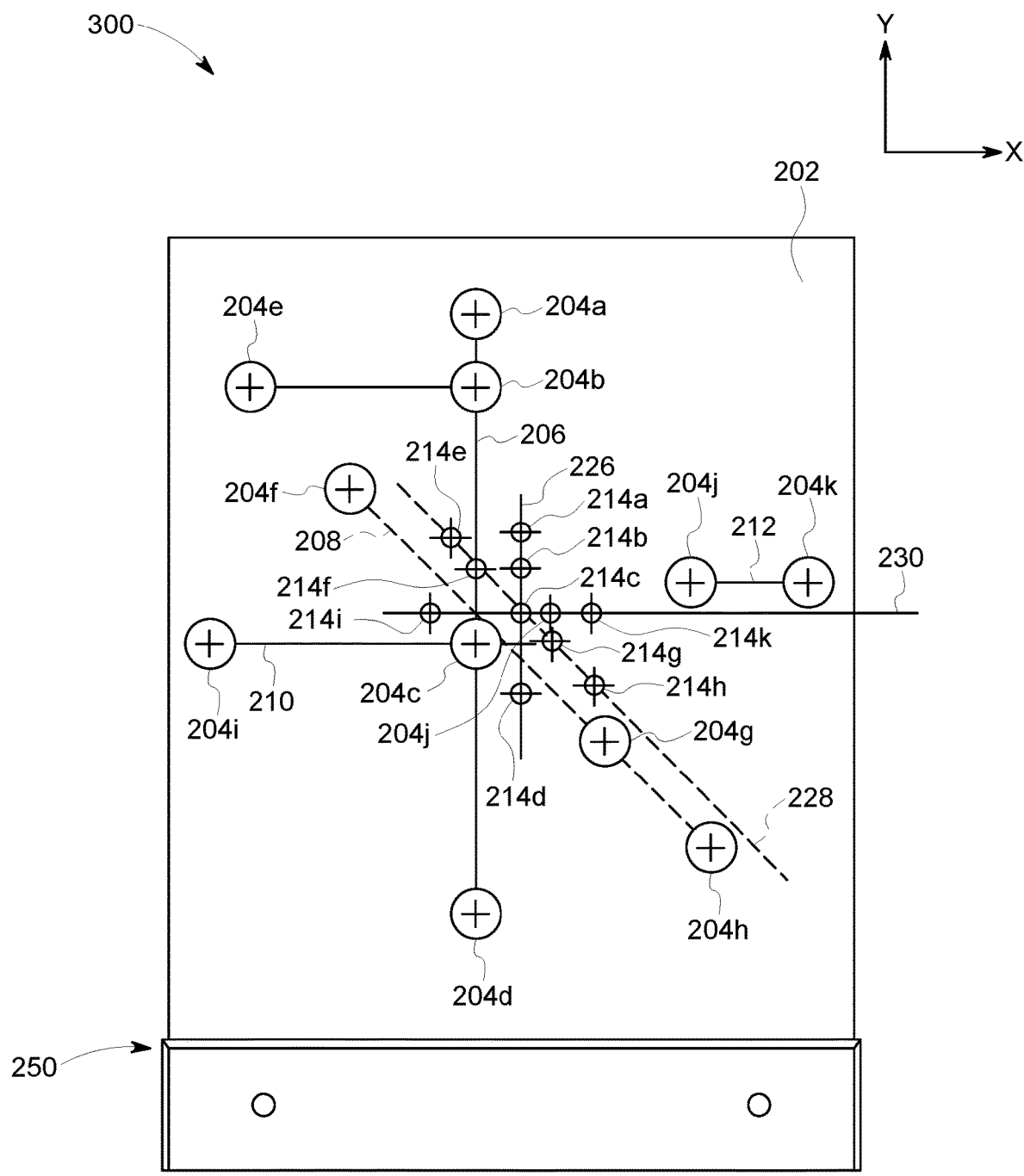
FIG. 3 is an illustration of arrangement of test objects in the phantom in FIG. 2.

FIG. 3 is an illustration of arrangement of test objects 204 and 214 in phantom 200. The first set of test objects 204 can include, for example, eleven spherical test objects 204a-k of similar radii that are arranged along various axes over the surface of the phantom 200. For example, test objects 204a-d can be arranged along a first axis 206, test objects 204f-h can be arranged along a second axis 208, test objects 204c and 204i can be arranged along a third axis 210, test objects 204j and 204k can be arranged along a fourth axis 212. The second set of test objects 214 can include eleven spherical test objects 214a-k of similar radii that are arranged along various axes over the surface of the phantom 200. For example, test objects 214a-d can be arranged along a fifth axis 226, test objects 214e-h can be arranged along a sixth axis 228, and test objects 214c and 214i-k can be arranged along a seventh axis 230. In one implementation, axes 208 and 228 can be substantially parallel. In another implementation, axes 210, 212 and 230 can be substantially parallel.

Figure 4:
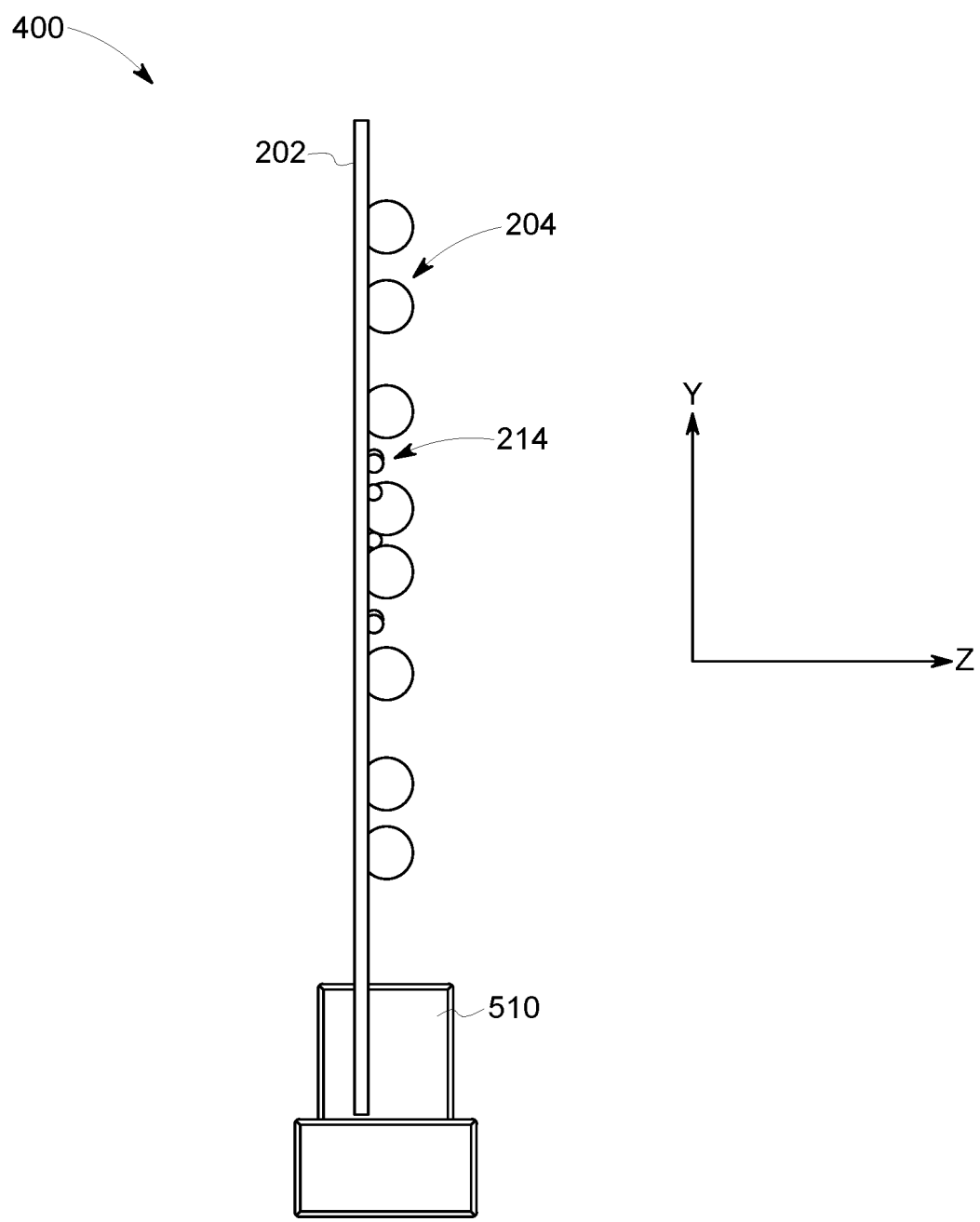
FIG. 4 is a side view of the phantom illustrated in FIG. 2.

FIG. 4 is the side view of the phantom 200 illustrated in FIG. 2. The test objects 204a-k and 214a-k can be coupled to the surface of the base 202 (e.g., rigidly attached). In one implementation, the radius of the test object 204a-k can range from about 5 mm to about 11.5 mm, and the radius of the test object 214a-k can be about 2 mm. The thickness of the base 202 can be about 2 mm. The base 202 can be attached to a support structure 510. The phantom 200 can be coupled (e.g., rigidly coupled) to a rotating platform via the support structure 510. The rotating platform can rotate the phantom 200 about they axis.

Figure 5:
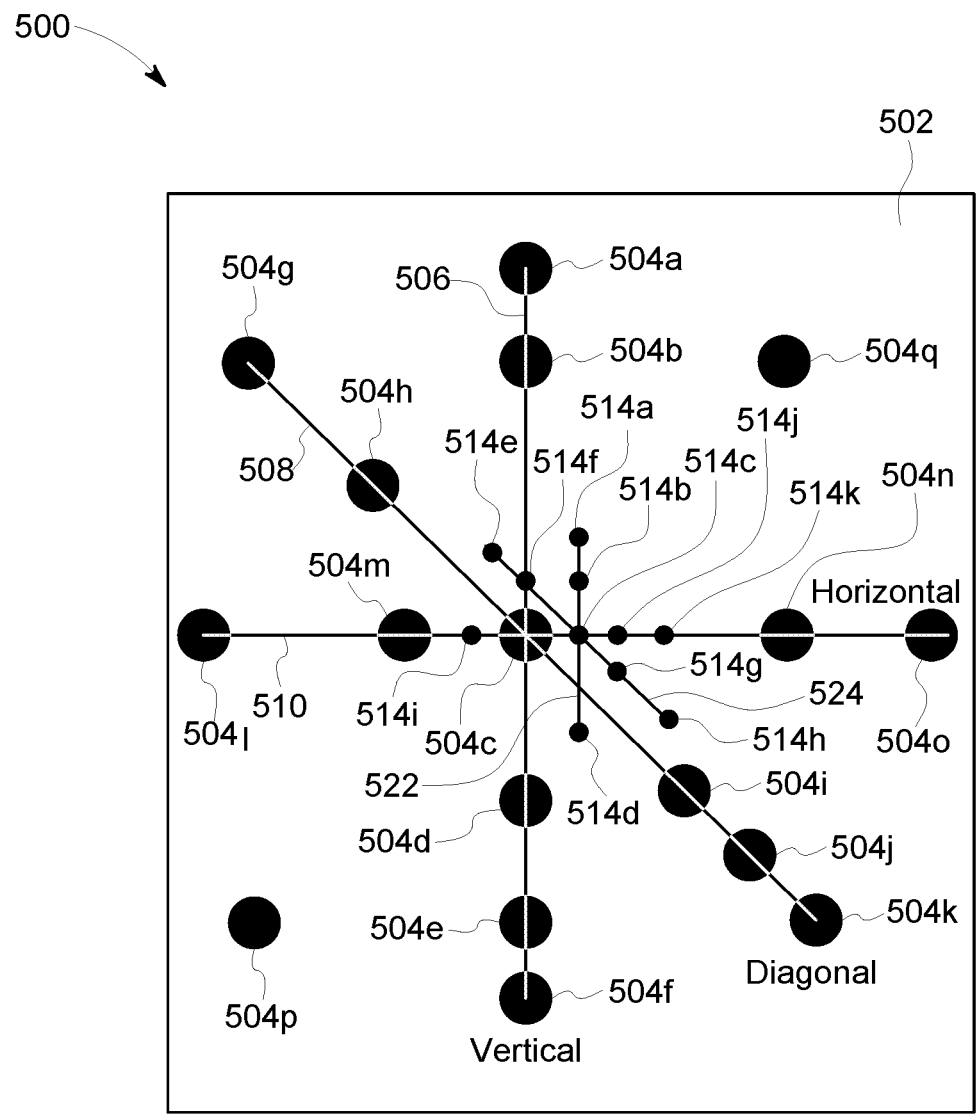
FIG. 5 is an illustration of an exemplary phantom.
Figure 6:
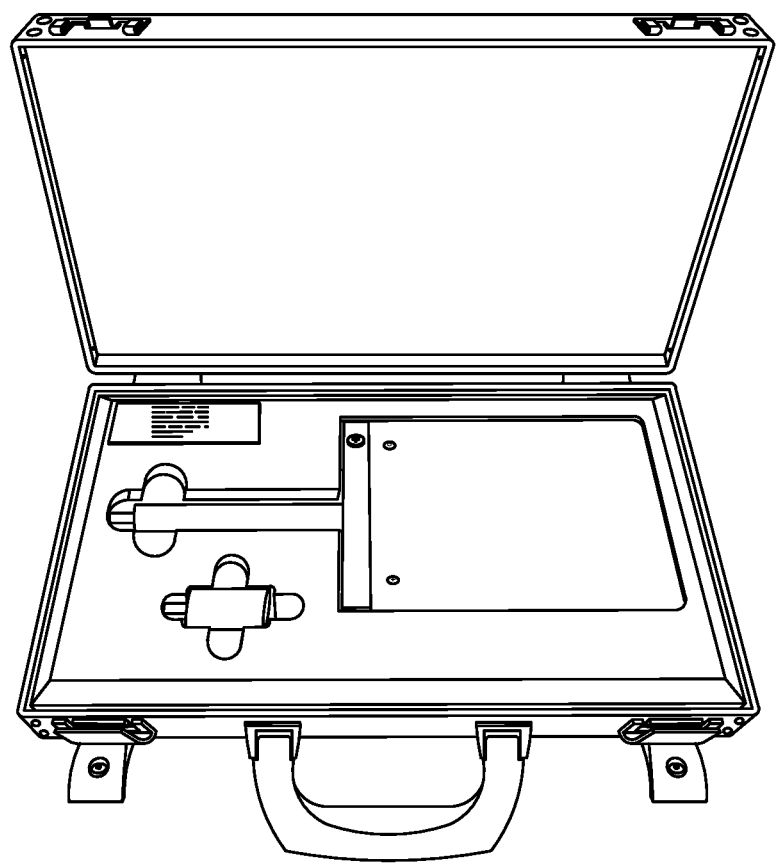
FIG. 6 is an illustration of phantom in FIG. 2 placed in a storage case.

FIG. 5 is an illustration of an exemplary phantom 500. The phantom 500 includes test objects 504 and 514 arranged on base 502 (e.g., rigidly attached). The first set of test objects 504 can include seventeen spherical test objects 504a-q of similar radii that can be arranged along various axes over the surface of the phantom 500. For example, test objects 504a-f can be arranged along a first axis 506, test objects 504g-k and 504c can be arranged along a second axis 508, and test objects 504c and 504l-o can be arranged along a third axis 510. The second set of test objects 514 can include eleven spherical test objects 514a-k of similar radii that are arranged along various axes over the surface of the phantom 500. For example, test objects 514a-d can be arranged along a fifth axis 522, test objects 514e-h can be arranged along a sixth axis 524, and test objects 514c and 514i-k can be arranged along the third axis 510. In one implementation, axes 506 and 522 can be parallel. In one implementation, axes 508 and 524 can be parallel. FIG. 6 is an illustration of phantom 200 placed in a storage case.

Figure 7:
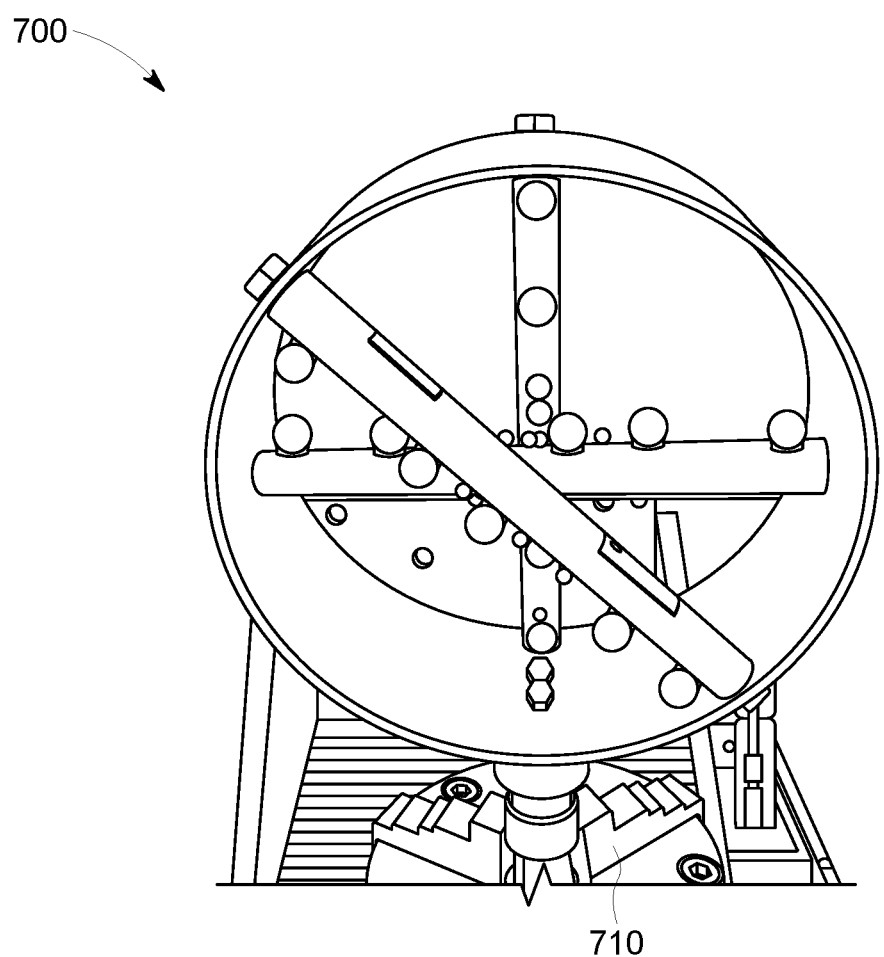
FIG. 7 is an image of an exemplary ball bar phantom.

FIG. 7 is an image of an exemplary phantom 700. The phantom 700 can include test objects having different geometries coupled to supports (or axes) that can be oriented horizontally, vertically and diagonally. The test objects can include a first set of test objects (e.g., spheres) having a first radius, and a second set of test objects having a second radius. The phantom 700 can be rotatably coupled to a base 710, The phantom 700 can be rotated about a vertical axis (e.g., y-axis), for example, by an actuator.

Figure 8:
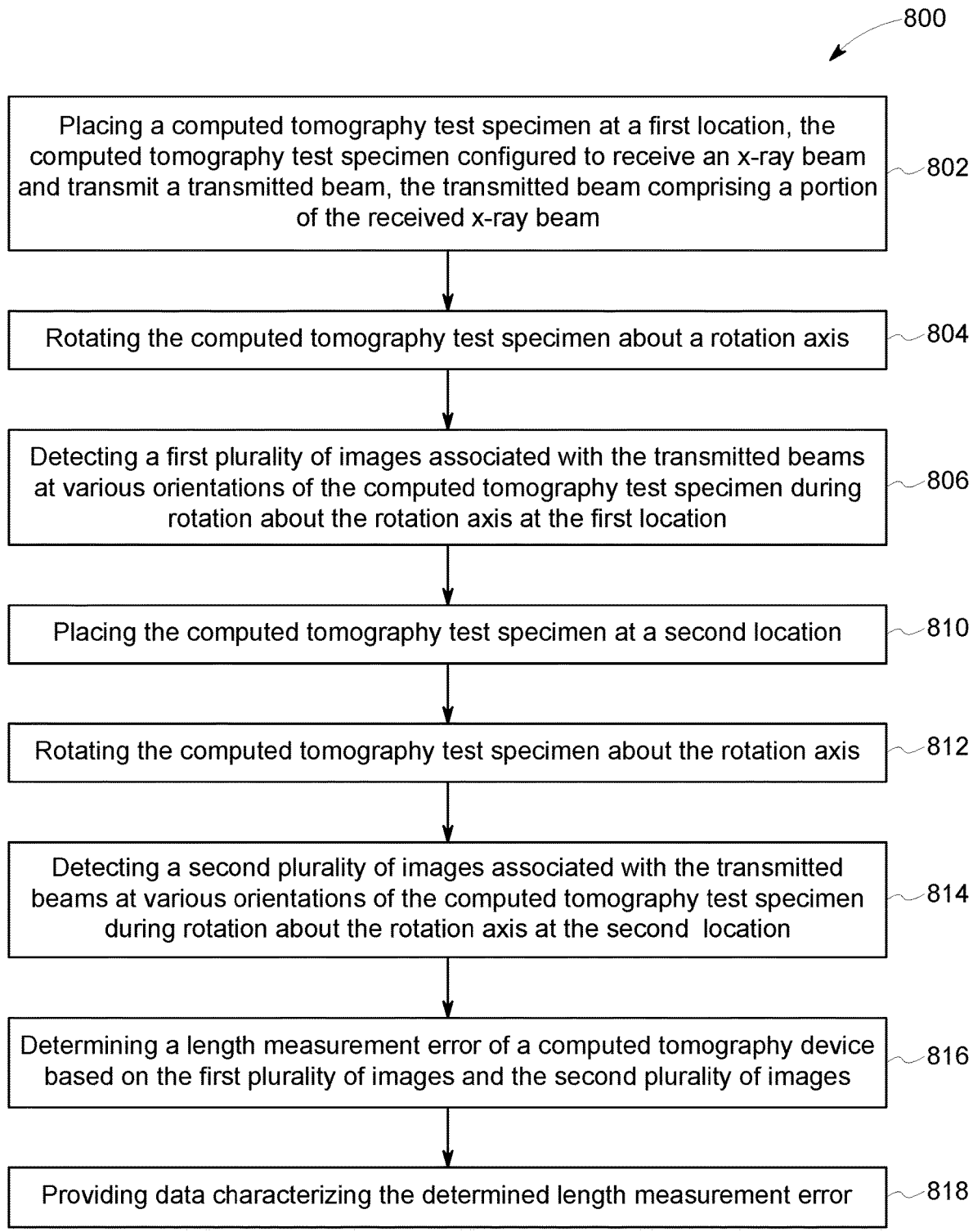
FIG. 8 is a flowchart illustrating an exemplary method for determining length error measurement of a computed tomography device.

FIG. 8 is a flowchart illustrating an exemplary method 800 for determining length measurement error of computed tomography device (e.g., CT system 100). At 802, a computed tomography test specimen (e.g., phantom 200, 500, and the like) can be placed at a first location (e.g., at location z1 situated between the radiation source 102 and detector 108 in FIG. 1). The test specimen can be radiated with an X-ray beam (e.g., 106a) emanating by a radiation source (e.g., radiation source 102). The test specimen can transmit at least a portion of the irradiated X-ray beam (e.g., 106b).

At 804, the test specimen can be rotated about a rotation axis at the first location. For example, in FIG. 1, the test specimen 104 (e.g., phantom 200, 500, and the like) can rotate about the y-axis at the location z1. At 806, a first plurality of images associated with the modified beams at various orientations (e.g., at various rotational angles) of the test specimen are detected during rotation about the rotation axis at the first location. For example, as the test specimen rotates (e.g., at a constant angular velocity) the detector 108 can intermittently (e.g., at a fixed time interval) capture the modified beam as multiple images that correspond to multiple rotational angle.

At 810, the test specimen is placed at a second location (e.g., at location z2 situated between the radiation source 102 and detector 108). The test specimen is irradiated with an X-ray beam emanating by the radiation source (e.g., radiation source 102), and can transmit a modified beam (e.g., modified electromagnetic radiation 106b). At 812, the test specimen can be rotated about a rotation axis at the second location. For example, in FIG. 1, the test specimen (e.g., phantom 200, 500, and the like) can rotate about the y-axis at the location z2. At 814, a second plurality of images associated with the modified beams at various orientations of the computed tomography test specimen are detected during rotation about the rotation axis at the second location. For example, as the test specimen rotates (e.g., at a constant angular velocity) the detector 108 can intermittently (e.g., at a fixed time interval) capture the modified beam in multiple images that correspond to multiple rotational angle.

At 816, a length measurement error of a computed tomography device can be determined based on the first plurality of images and the second plurality of images. The length measurement error can be determined, for example, based on measured deviations in the size of one or more test objects (e.g. between a maximum and a minimum value), distance between test objects and deviations in the shape of one or more test objects. At 818, the length measurement error can be provided. For example, the length determination error can be saved in a database and/or presented to an operator.

Figure 9:
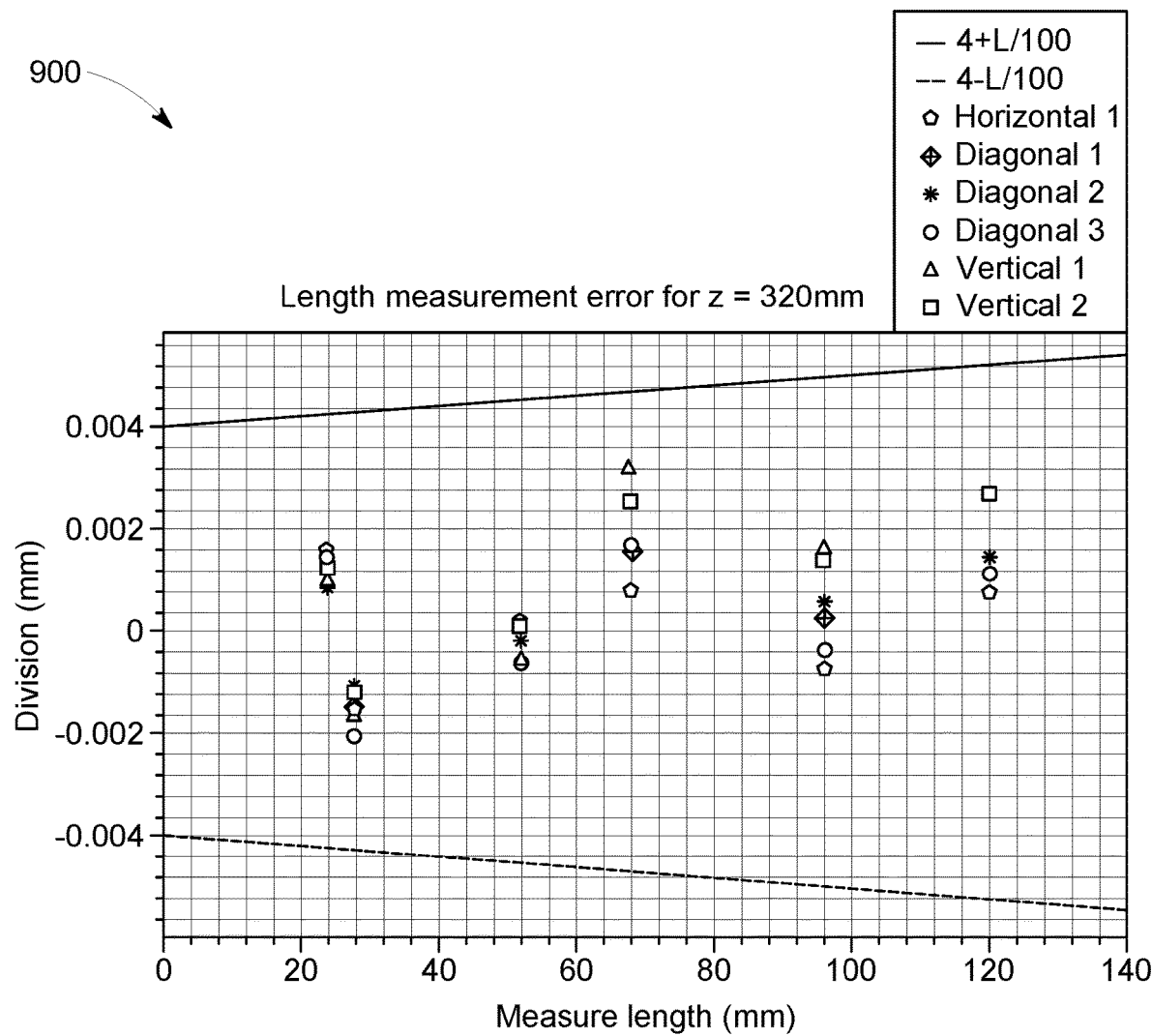
FIG. 9 is a plot of exemplary sphere distance (SD) error measurements of large spheres of the ball bar phantom in FIG. 7.
Figure 10:
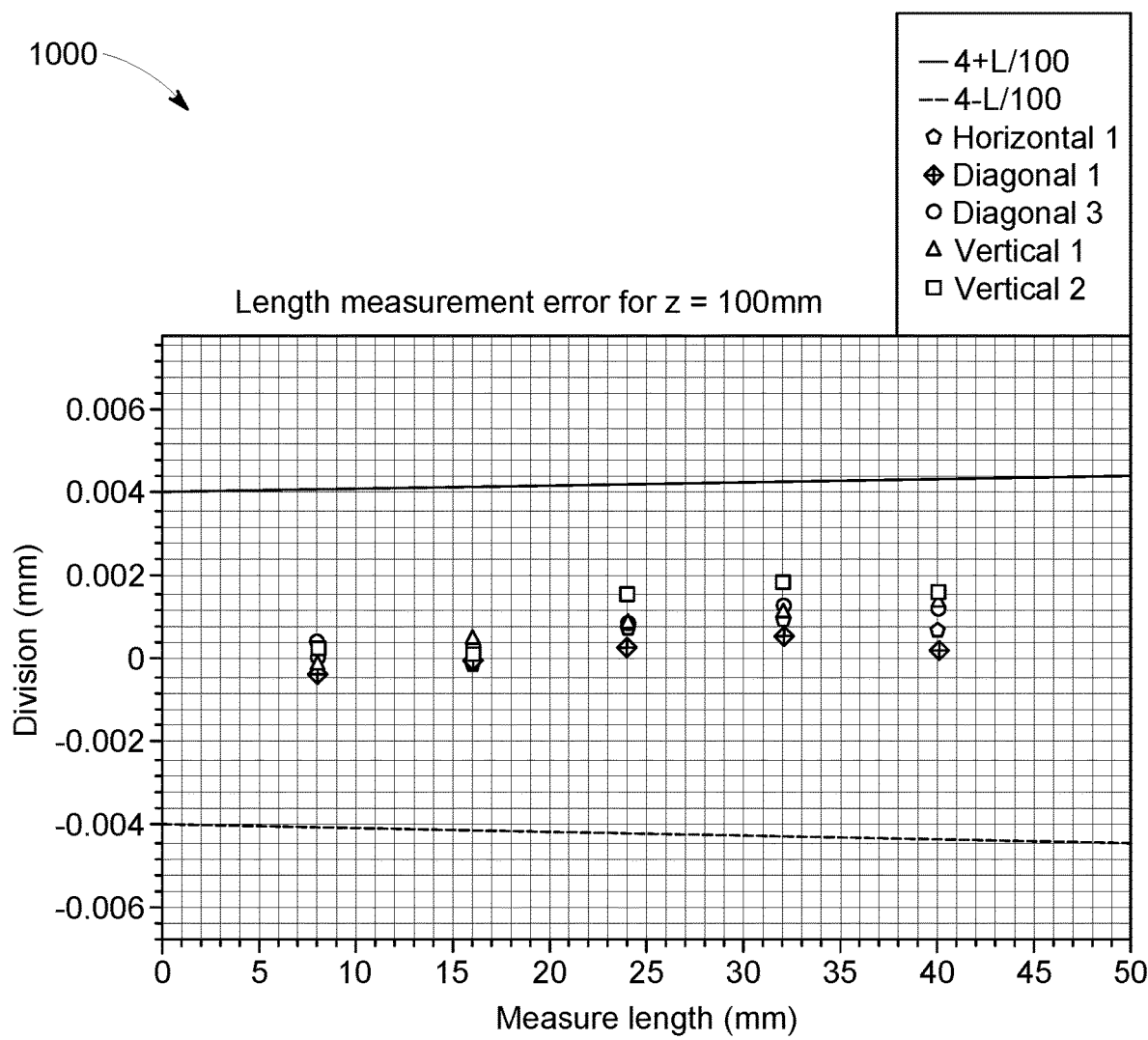
FIG. 10 is a plot of exemplary SD error measurements of small spheres of the ball bar phantom in FIG. 7.

FIG. 9 is a plot of exemplary sphere distance (SD) error measurements of large spheres of a ball bar phantom (e.g., phantom 700). One or more SD error measurements can be performed along a horizontal direction (e.g., parallel to the x-z plane), along a vertical direction (e.g., perpendicular to the x-z plane), and along a diagonal direction (e.g., parallel to the x-y plane). FIG. 10 is a plot of exemplary SD error measurements of small spheres of a ball bar phantom (e.g., phantom 700).

Figure 11:
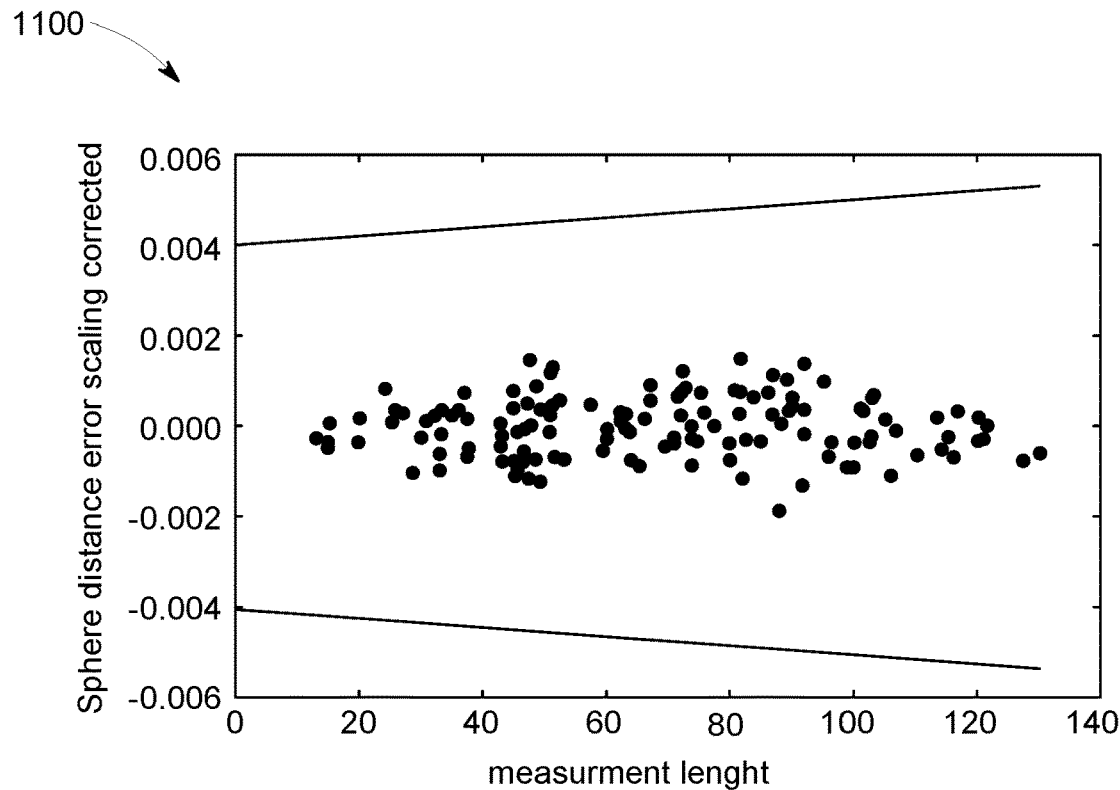
FIG. 11 is a plot of exemplary sphere distance error measurement for large spheres in FIG. 5.
Figure 12:
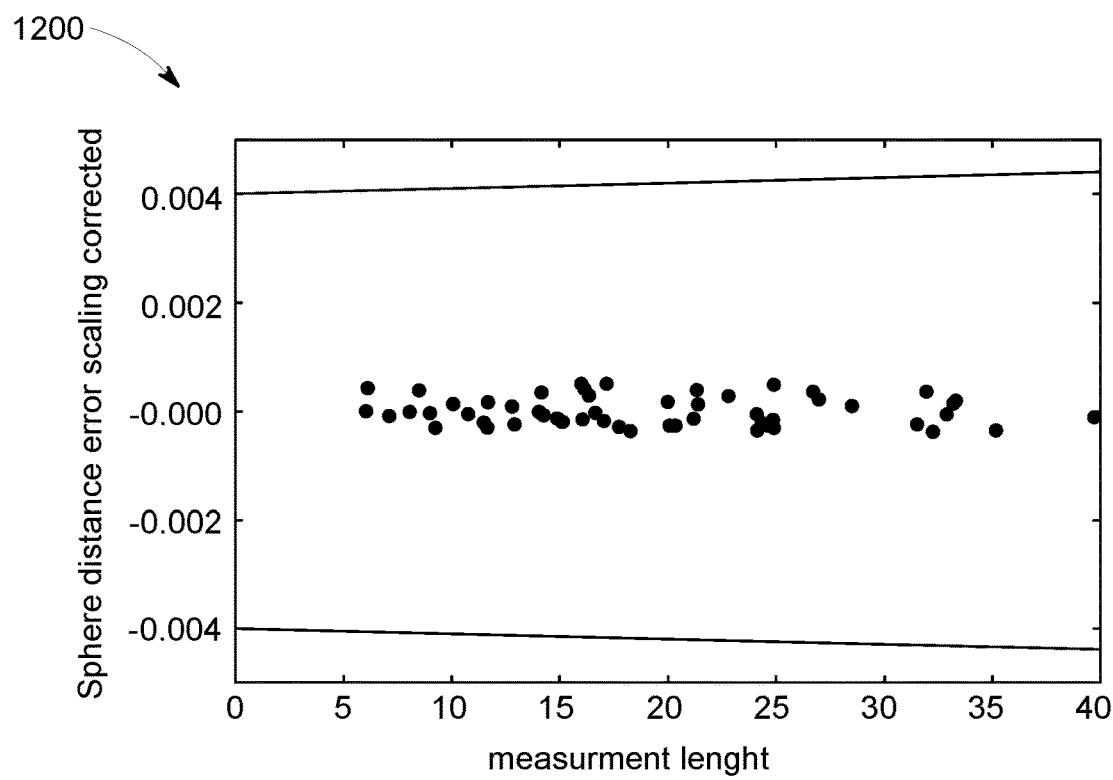
FIG. 12 is a plot of exemplary sphere distance error measurement for small spheres in FIG. 5.

FIG. 11 is a plot of exemplary sphere distance error measurement for large spheres in phantom 500. One or more SD error measurements can be performed along a horizontal direction (e.g., parallel to the x-z plane), along a vertical direction (e.g., perpendicular to the x-z plane), and along a diagonal direction (e.g., parallel to the x-y plane). FIG. 12 is a plot of exemplary sphere distance error measurement for small spheres in phantom 500.

Although a few variations have been described in detail above, other modifications or additions are possible. For example, test objects can have multiple sizes. For example, test objects can be spheres of different sizes (e.g. radii ranging from 0.25 mm to about 360 mm). The spacing between test objects along a given axis can be varied.

The subject matter described herein can provide one or more technical advantages. The test specimen can include material (e.g., ceramics) whose properties (e.g., density, optical properties, shape, and the like) may not vary considerably during one or more phantom calibration processes. For example, distances between test objects (e.g., 202, 204, etc.) my not change considerably due to material alteration between the phantom calibration processes. This can allow for longer phantom calibration intervals (e.g., time durations between multiple phantom calibration processes). This can also reduce phantom calibration errors and/or prevent repetition of phantom calibration measurement. System calibration or accuracy verification errors can also be reduced because arrangement of test objects (e.g., test objects of different sizes) in various geometries can limit/reduce the adjustment of test specimen by hand or other means. Reduction in the adjustment of test objects by hand can also reduce the time needed to calibrate or verify accuracy of the CT system. The test specimen can allow for a faster calibration or accuracy verification process. In some implementations, for example, measurement along vertical, diagonal and horizontal axes can be performed simultaneously. This can reduce the calibration or accuracy verification time by about three times. Test specimen made of ceramics can be cheaply produced.

Exemplary embodiments described herein provide an overall understanding of the principles of the structure, function, manufacture, and use of the systems, devices, and methods disclosed. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

Other embodiments are within the scope and spirit of the disclosed subject matter. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device; e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software; firmware; hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

What is claimed is:

1. An apparatus comprising:
   a base structure;
   a first set of test objects arranged along a first axis and coupled to the base structure;
   a second set of test objects arranged along a second axis and coupled to the base structure, wherein the first set of test objects and the second set of test objects have a first geometry;

a third set of test objects arranged along a third axis and coupled to the base structure; and
a fourth set of test objects arranged along a fourth axis and coupled to the base structure, wherein the third set of test objects and the fourth set of test objects have a second geometry different from the first geometry,
wherein locations of the first set of test objects, the second set of test objects, the third set of test objects, and the fourth set of test objects are spatially fixed with respect to the base structure, and
wherein the apparatus is a test specimen adapted for one or more of calibration and accuracy verification of computed tomography system.

2. The apparatus of claim 1, wherein the base structure is a ceramic plate.

3. The apparatus of claim 1, wherein the first axis is parallel to the third axis, the second axis is parallel to the fourth axis.

4. The apparatus of claim 1, wherein the first set of test objects and the second set of test objects are spherical having a first radius, and the third set of test objects and the fourth set of test objects are spherical having a second radius different from the first radius.

5. The apparatus of claim 4, wherein the first set of test objects, the second set of test objects, the third set of test objects and the fourth set of test objects include ruby and/or ceramic.

6. The apparatus of claim 4, wherein a value of the first radius is 5 mm, and a value of the second radius is 2 mm.

7. The apparatus of claim 1, wherein the base structure, the first set of test objects, the second set of test objects, the third set of test objects, and the fourth set of test objects are configured to receive X-ray radiation from a source and modify a portion of the received X-ray radiation.

8. The apparatus of claim 1, further comprising:
a pair of test objects having the first geometry and arranged along a fifth axis; and
a first test object from the first set of test objects and a second test object are arranged along a sixth axis,
wherein the fifth axis and the sixth axis are parallel and the second test object has the first geometry.

9. The apparatus of claim 8, wherein eleven test objects have the first geometry, and eleven test objects have the second geometry.

10. The apparatus of claim 1, further comprising:
a seventh set of test objects arranged along a seventh axis and coupled to the base structure; and
an eighth set of test objects arranged along an eighth axis and coupled to the base structure,
wherein the seventh set of test objects have the first geometry, and the eighth set of test objects have the second geometry.

11. The apparatus of claim 1, wherein the first geometry includes a shape of the first set of test objects and the second geometry includes a shape of the second set of test objects.

12. A method comprising:
placing a computed tomography test specimen at a first location, the computed tomography test specimen configured to receive an X-ray beam and transmit a modified beam, the modified beam comprising a portion of the received X-ray beam;
rotating the computed tomography test specimen about a rotation axis
detecting a first plurality of images associated with the modified beam at various orientations of the computed tomography test specimen during rotation about the rotation axis at the first location;
placing the computed tomography test specimen at a second location;
rotating the computed tomography test specimen about the rotation axis;
detecting a second plurality of images associated with modified beams at various orientation of the computed tomography test specimen during rotation about the rotation axis at the second location;
determining a length measurement error of a computed tomography device based on the first plurality of images and the second plurality of images; and
providing data characterizing the determined length measurement error,
wherein the computed tomography test specimen includes:
a base structure;
a first set of test objects arranged along a first axis and coupled to the base structure;
a second set of test objects arranged along a second axis and coupled to the base structure, wherein the first set of test objects and the second set of test objects have a first geometry;
a third set of test objects arranged along a third axis and coupled to the base structure; and
a fourth set of test objects arranged along a fourth axis and coupled to the base structure, wherein the third set of test objects, and the fourth set of test objects have a second geometry different from the first geometry,
wherein locations of the first set of test objects, the second set of test objects, the third set of test objects, and the fourth set of test objects are spatially fixed with respect to the base structure.

13. The method of claim 12, wherein the base structure is a ceramic plate.

14. The method of claim 12, wherein the rotation axis of the computed tomography test specimen is perpendicular to a path of the X-ray beam.

15. The method of claim 12, wherein the first set of test objects and the second set of test objects are spherical having a first radius, and the third set of test objects and the fourth set of test objects are spherical having a second radius different from the first radius.

16. The method of claim 15, wherein the first set of test objects, the second set of test objects, the third set of test objects and the fourth set of test objects include ruby and/or ceramic.

17. The method of claim 15, wherein a value of the first radius is 5 mm, and a value of the second radius is 2 mm.

18. The method of claim 12, wherein the computed tomography test specimen further comprises:
a pair of test objects having the first geometry and arranged along a fifth axis; and
a first test object from the first set of test objects and a second test object arranged along a sixth axis,
wherein the fifth axis and the sixth axis are parallel and the second test object has the first geometry.

19. The method of claim 12, wherein the computed tomography test specimen further comprises:
a seventh set of test objects arranged along a seventh axis and coupled to the base structure; and
an eighth set of test objects arranged along an eighth axis and coupled to the base structure, and
wherein the seventh set of test objects have the first geometry, and the eighth set of test objects have the second geometry.

20. The method of claim 12, wherein the computed tomography test specimen further comprises:
- a pair of test objects having the first geometry and arranged along a fifth axis; and
- a first test object from the first set of test objects and a second test object are arranged along a sixth axis, wherein the fifth axis and the sixth axis are parallel and the second test object has the first geometry.

\* \* \* \* \*